United States Patent
Bernhardt

(10) Patent No.: US 9,730,668 B2
(45) Date of Patent: Aug. 15, 2017

(54) METHOD FOR OPERATING A COMPUTED TOMOGRAPH AND A COMPUTED TOMOGRAPH

(71) Applicant: Philipp Bernhardt, Forchheim (DE)

(72) Inventor: Philipp Bernhardt, Forchheim (DE)

(73) Assignee: Siemens Aktiengesellschaft, München (DE)

( * ) Notice: Subject to any disclaimer, the term of this patent is extended or adjusted under 35 U.S.C. 154(b) by 38 days.

(21) Appl. No.: 14/734,162

(22) Filed: Jun. 9, 2015

(65) Prior Publication Data

US 2015/0359503 A1 Dec. 17, 2015

(30) Foreign Application Priority Data

Jun. 11, 2014 (DE) .......... 10 2014 211 150

(51) Int. Cl.
*A61B 6/00* (2006.01)
*A61B 6/03* (2006.01)

(52) U.S. Cl.
CPC .......... *A61B 6/542* (2013.01); *A61B 6/032* (2013.01); *A61B 6/5258* (2013.01)

(58) Field of Classification Search
None
See application file for complete search history.

(56) References Cited

U.S. PATENT DOCUMENTS

| 5,379,333 | A | 1/1995 | Toth |
| 6,507,639 | B1 | 1/2003 | Popescu |
| 8,699,658 | B2 * | 4/2014 | Yu .......... A61B 6/032 378/16 |
| 2005/0254621 | A1 * | 11/2005 | Kalender ......... A61B 6/032 378/46 |

(Continued)

FOREIGN PATENT DOCUMENTS

| DE | 19737408 A1 | 3/1998 |
| DE | 102005021020 A1 | 11/2006 |

OTHER PUBLICATIONS

"CT Dose Reduction and Dose Management Tools: Overview of Available Options" by Cynthia H. McCollough, Michael R. Bruesewitz, and James M. Kofler in the journal RadioGraphics, 26:503-512, 2006.

*Primary Examiner* — Michael Logie
(74) *Attorney, Agent, or Firm* — Lempia Summerfield Katz LLC

(57) ABSTRACT

A method for operating a computed tomograph is provided, wherein an X-ray penetrates an object from different positions, a deposition of an individual dose is effected in at least one part of the object, and an image signal is generated in the detector by way of a transmitted intensity of the X-ray, wherein exposure-related parameters for the respective different positions are individually set such that with respect to a specific position, the share of the associated individual dose is raised if a raising of the individual dose in the specific position brings about a greater improvement in the (Continued)

image quality than in another position, or the share of the associated individual dose is lowered if a lowering of the individual dose in the specific position brings about a smaller deterioration in the image quality than in another position, in order to lower stochastic risks for mutations and uncontrolled cell growth.

11 Claims, 2 Drawing Sheets

(56) References Cited

U.S. PATENT DOCUMENTS

| | | | | |
|---|---|---|---|---|
| 2006/0072705 | A1* | 4/2006 | Munro | G21K 1/10 378/159 |
| 2006/0251213 | A1* | 11/2006 | Bernhardt | A61B 6/00 378/62 |
| 2007/0189438 | A1* | 8/2007 | Popescu | A61B 6/025 378/4 |
| 2008/0232542 | A1* | 9/2008 | Lin | A61B 6/542 378/16 |
| 2010/0303196 | A1* | 12/2010 | Zou | A61B 6/032 378/5 |
| 2012/0238795 | A1* | 9/2012 | Bert | A61N 5/1043 600/1 |
| 2014/0031603 | A1* | 1/2014 | Robar | A61N 5/1049 600/1 |
| 2014/0328447 | A1* | 11/2014 | Koweek | A61B 6/405 378/4 |
| 2014/0362971 | A1* | 12/2014 | Lee | G21K 1/10 378/16 |
| 2015/0063536 | A1* | 3/2015 | Kobayashi | A61B 6/032 378/20 |

* cited by examiner

METHOD FOR OPERATING A COMPUTED TOMOGRAPH AND A COMPUTED TOMOGRAPH

CROSS-REFERENCE TO RELATED APPLICATIONS

This application claims the benefit of DE 10 2014 211 150.1, filed on Jun. 11, 2014, which is hereby incorporated by reference in its entirety.

TECHNICAL FIELD

The embodiments relate to a method for operating a computed tomograph, in which an X-ray penetrates an object from different positions and in which, in the different positions, respectively, both a deposition of an individual dose is effected in at least one part of the object and also, by an exposure of a detector, an image signal is generated in the detector by way of a transmitted intensity of the X-ray, wherein the individual doses add up to a total dose. The embodiments also relate to a computed tomograph configured to carry out such a method.

BACKGROUND

Three-dimensional (3D) reconstructions are being employed increasingly frequently in medical X-ray-based imaging. This involves reconstructing a 3D volume from a plurality of projection images from various directions or angulations, which is to say in different positions. This is classically carried out on special computed tomographs, but in the meantime it is also the state of the art on so-called C-arm machines. In the case of such a procedure, a so-called rotational scan, attention is paid primarily, in terms of a patient's dose uptake, to an actual total dose, that is to say the dose, in particular the cumulative dose, that primarily impacts the patient's internal organs. This total dose is responsible for possible stochastic risks. In other words, a raising of the total dose results in an increase in the risk of mutations and uncontrolled cell growth, commonly known as "cancer". Deterministic damage at a skin entry point, as is attended to primarily in the case of classical two-dimensional (2D) projection imaging, is less significant in this case since the radiation entry zone is constantly being changed due to the switching into different positions.

According to the present-day state of the art, most X-ray machines now have automatic exposure regulation. An exposure regulation system may set five parameters: a tube voltage, a tube current, the exposure time per image or position, a prefiltering parameter, and an emitter size or a focus. In this regard, the selection of the parameters strongly influences the accumulating total dose for the patient, and also the resultant image quality both for two-dimensional projection images and also a three-dimensional reconstruction. In this regard, the influence of the current and exposure time is quantifiable: raising these has a linear effect on actual dose and image quality. The image quality may be described, for example, by the square of the signal-to-noise ratio (SNR) or a contrast ratio. Raising the X-ray voltage, on the other hand, increases the actual dose, or the actual individual dose per position and also the actual total dose, more than proportionally since deeper layers may be reached and higher quanta of energy are used. The effects of this parameter on image quality, on the other hand, are strongly dependent on the conditions. Furthermore, an important factor for image quality is of course the total number of quanta in fact transmitted and reaching a detector or image receiver forming part of the computed tomograph.

DE 197 37 408 A1 describes a method and a device for modulating an X-ray current in a computed tomography system. In this regard, a desired noise level for a final image is selected, and a desired minimal X-ray photon measured value and also a desired average X-ray photon measured value identified, with which an image corresponding to the desired noise level may be generated. During a scan, prevailing X-ray photon measured values are compared with the desired average X-ray photon measured values at different projection angles and used to generate an X-ray modulation factor. This modulation factor is then used to modulate the X-ray tube current.

U.S. Pat. No. 6,507,639 B1 describes a method for modulating a radiation dose of an X-ray tube, which is dependent on an angle of rotation of a drum bearing on which the X-ray tube is arranged. In this regard, the modulation is carried out such that an instantaneous intensity of the X-ray radiation likewise reaches its maximum at the time of a maximal absorption of the X-rays by a patient and not at some other time.

DE 10 2005 021 020 A1 describes a method for calculating an orthogonal X-ray attenuation of an object supported on an object table of a computed tomograph on the basis of a measured reference X-ray attenuation. For the purpose of saving on X-ray dose, the projection angle-dependent fluctuation in the attenuation is partly offset by configuration of the radiation intensity generated by the X-ray emitter.

U.S. Pat. No. 5,379,333 A describes an X-ray computed tomograph in which a current of an X-ray tube is modulated as a function of a drum bearing angle in order to reduce a total dose for the patient without significantly raising the image noise in the process. To do this, test pictures are made and the absorption of the X-ray radiation by the patient determined in two orthogonal directions. A modulation profile is then calculated, according to which the X-ray current is modulated during image capture, in which the X-ray tube is rotated around the patient. In this regard, the modulation may be effected according to a sine or a cosine wave.

The article "CT Dose Reduction and Dose Management Tools: Overview of Available Options," by Cynthia H. McCollough, Michael R. Bruesewitz, and James M. Kofler in the journal RadioGraphics, 2006, Vol. 26, pp. 503-512, provides an overview of opportunities for lowering an X-ray dose in computed tomography. The possibility, inter alia, of varying an X-ray current while the X-ray tube is rotating around a patient is examined in this regard. Starting with a constant tube current, the current is modulated sinusoidally in this process.

SUMMARY AND DESCRIPTION

The scope of the present invention is defined solely by the appended claims and is not affected to any degree by the statements within this summary. The present embodiments may obviate one or more of the drawbacks or limitations in the related art.

The object of the embodiments is to obtain a best possible image quality with a lowest possible radiation uptake for a patient during computed tomography.

In the case of a method for operating a computed tomograph, an X-ray of the computed tomograph penetrates an object, (e.g., a patient or a part of a patient), from different positions. These positions are frequently also referred to as angulations since in the different positions, the X-ray may penetrate the object at a different angle in each case. In the different positions, respectively, a deposition of an individual dose is effected in at least one part of the object. The individual dose may include, in particular, an actual dose, and the part of the object, in particular, an organ of a patient. In this regard, the individual doses add up to a total dose. In the different positions, in addition, by an exposure of a detector, an image signal is generated in the detector by way of a transmitted intensity of the X-ray.

In order to lower stochastic risks, at least one exposure-related parameter of the detector is set in each case for the respective different positions and therefore the associated individual doses to be deposited, which influence an image quality of the image signal. If a plurality of exposure parameters is set, the parameters may be set individually and differently for each position in each case. The individual doses to be deposited may therefore be set with the aid of a model that establishes a connection between radiation parameters, and therefore the exposure parameters, and a dose deposited in a test. This is effected such that, with respect to a specific position, the share of the associated individual dose in the total dose is raised if a raising of the individual dose in the predetermined position brings about a greater improvement in the image quality than in another position, or with respect to the specific position, the share of the associated individual dose in the total dose is lowered if a lowering of the individual dose in the specific position brings about a smaller deterioration in the image quality than in another position. A raising of the individual dose is therefore undertaken in the specific position if the amount of raising of the individual dose in the specific position brings about a greater improvement in the image quality than in another position, or a lowering of the individual dose is undertaken in the specific position if the amount of lowering of the individual dose in another position brings about a greater deterioration in the image quality than in the specific position.

In one or a plurality of positions or angulations with an object-specifically high X-ray absorption, at which a relatively large dose amount has to be invested in order to obtain an image that is to some extent good, this image quality is therefore deliberately relinquished in order to use the correspondingly saved dose amount in one or a plurality of positions in which it is fundamentally easier to produce a good image than with a comparatively lower actual dose, as may be the case for positions with a low X-ray absorption. In this regard, the total dose may be predefined so that a proportional distribution of the predefined total dose into the individual doses is obtained, in order to generate, with this predefined total dose, a reconstructed three-dimensional image with the improved or best possible quality. Alternatively, a specific image quality may also be predefined for the reconstructed three-dimensional image, which is obtained with a lowered or lowest possible total dose. This has the advantage that the stochastic risks of mutations and uncontrolled cell growth are reduced for an unchanged image quality of the three-dimensional reconstruction, or the quality of the three-dimensional reconstruction is improved for a certain accepted risk of this type. The proposed method may also be combined with existing methods without any limitation.

The raising or lowering may be effected in percentage terms of the total dose so that a raising of an individual dose automatically entails a lowering of other individual doses and vice versa. It may also be carried out on an absolute basis, however, so that as an individual dose is raised, the total dose also increases, or as the individual dose is lowered, the total dose is also lowered.

In this regard, the raising and/or lowering may be effected in infinitesimal acts. This has the advantage that an optimal distribution of the individual doses may be determined accurately and, in particular, a build up to higher individual doses may be prevented.

One embodiment provides that the individual doses are raised and/or lowered starting from a predetermined default setting at which identical values are selected for the exposure parameter or parameters, in particular, for the different positions. Alternatively, in the case of the predetermined standard setting, a distribution of values for the exposure parameters may already be provided, that is to say, for example, a lower exposure time for positions in which the patient is irradiated from a front or rear side and longer exposure times for positions in which the patient is irradiated from one side. This has the advantage that the optimization of the individual doses, that is to say the respective raising or lowering of the individual doses for one or a plurality of positions, is standardized and therefore may be carried out particularly rapidly and with little effort.

One embodiment provides that the exposure parameters for the different positions are selected such that a respectively associated product of the individual dose and a measure for the image quality is identical for the different positions. The total dose is distributed in an optimal manner across the different positions. This may be achieved, for example, by carrying out the aforementioned optimization, that is to say the lowering and raising of the individual doses with infinitesimal changes, until an infinitesimal raising or lowering of an individual dose in all positions results in an equally large improvement or deterioration in the image quality. This has the advantage that in the case of a predefined total dose, a three-dimensional reconstruction is generated with the maximal quality, or in the case of a predefined image quality of the three-dimensional reconstruction, the quality is obtained with the lowest possible total dose.

A further form of embodiment provides that a signal-to-noise ratio, and in particular the square of a signal-to-noise ratio, is selected as a measure for the image quality. This has the advantage that the connection between image quality and the individual doses is thereby well-defined, so that it may be well modeled. An optimal apportionment of the individual doses is therefore in fact obtainable with the method, since classical methods may be applied for calculating an error propagation.

A further form of embodiment provides that one or more exposure parameters is/are a tube voltage and/or a tube current and/or an exposure time. The tube voltage may be used as the exposure parameter in this case since the voltage has a large influence on the individual doses in the various positions, that is to say for the various projections, with the result that, via a setting of the tube voltage, a radiation uptake of a patient with different absorption cross-sections for the X-ray may be saved. In this regard, a varying range, which is a consequence of a varying tube voltage, provides the effect that, in the case of the three-dimensional reconstruction, different energy-dependent absorptions and as a consequence, varying individual doses, have to be determined and certain assumptions have to be made about the nature of the object to be reconstructed in this regard. If the variation of the tube voltage is unfavorable in a given situation, therefore, then the optimal distribution of the individual doses may be approximated with a variation of the tube current and/or the exposure time.

Another form of embodiment provides that the individual doses to be deposited are set with account being taken of weighting factors for specific tissues, and in particular specific organs. This has the advantage that the individual doses and consequently the total dose that is ultimately deposited in a specific tissue or a specific organ plays a part in the optimization of the distribution of the individual doses, that is to say the raising or lowering of the individual doses in the different positions. Particular sensitivities with reference to the aforementioned stochastic risks are therefore taken into account. For example, a raising and lowering of the individual doses in the different positions may be carried out, therefore, on the condition that a specific organ, such as a stomach for example, is allowed to be subjected to a particularly low dose. On the other hand, the radiation uptake may thus also be raised in less sensitive tissues if the raising serves to improve the image quality. The dose-saving effect is also raised.

A further form of embodiment provides that the individual doses to be deposited are set with account being taken of a geometry of the object, and in particular an anatomy of a patient. This has the advantage that the dose-saving effect is raised.

Provision may furthermore be made that the total dose does not exceed a predetermined value. This has the advantage that a specific maximal stochastic risk may not be exceeded, and in particular, if the raising or lowering of the individual doses is effected on the basis of absolute values, with a predefined minimal size for example, a build up, that is to say an excessive raising of the total dose in the case of a repeated raising of individual doses, is avoided.

The embodiments also relate to a computed tomograph with a control unit, the computed tomograph configured to penetrate an object with an X-ray from different positions and in the different positions, respectively, by an exposure of a detector of the computed tomograph, to capture an image signal in the detector by way of a transmitted intensity of the X-ray. In the different positions, respectively, a deposition of an individual dose is effected in at least one part of the object and the individual doses add up to a total dose. In order to lower stochastic risks, the control unit is configured in this regard to set individually in each case one or a plurality of exposure-related parameters for the respective different positions and therefore the associated individual doses to be deposited, which influence an image quality of the image signal. In fact, with respect to a specific position, the share of the associated individual dose in the total dose is raised if a raising of the individual dose in the specific position brings about a greater improvement in the image quality than in another position. Alternatively, with respect to the specific position, the share of the associated individual dose in the total dose is lowered if a lowering of the individual dose in the specific position brings about a smaller deterioration in the image quality than in another position. The advantages obtained thereby correspond to the advantages of the described method. The features and advantages of the described forms of embodiment of the method also apply respectively to the computed tomograph.

All the features and feature combinations referred to in the preceding description and also the features and feature combinations referred to in the description of the figures and/or depicted alone in the figures in the following may be used not only in the respectively indicated combination but also in other combinations or on their own without departing from the scope of the embodiments. Embodiments that are not explicitly depicted and explained in the figures, but arise and may be generated from the explained embodiments through separate feature combinations are therefore also to be regarded as included and disclosed.

DETAILED DESCRIPTION

Figure 1:
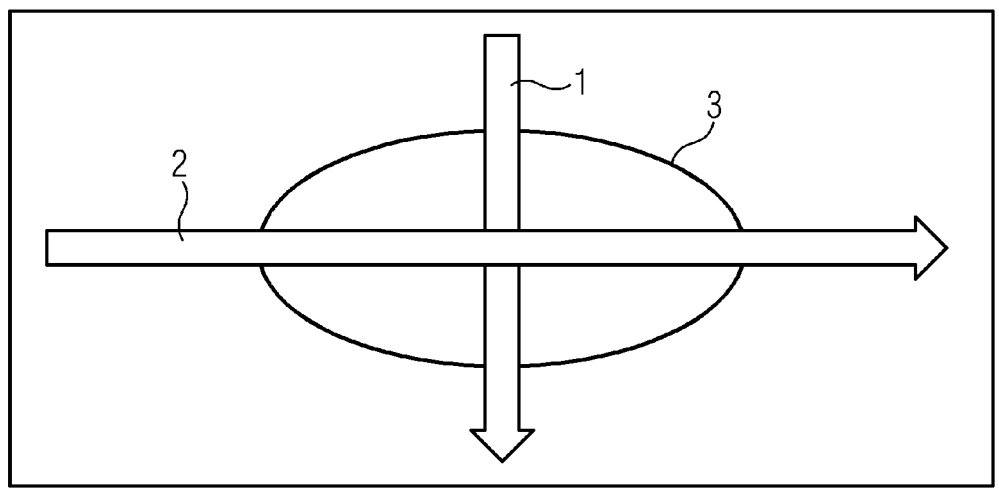
FIG. 1 depicts an object that is being irradiated according to an example of the method.
Figure 2:
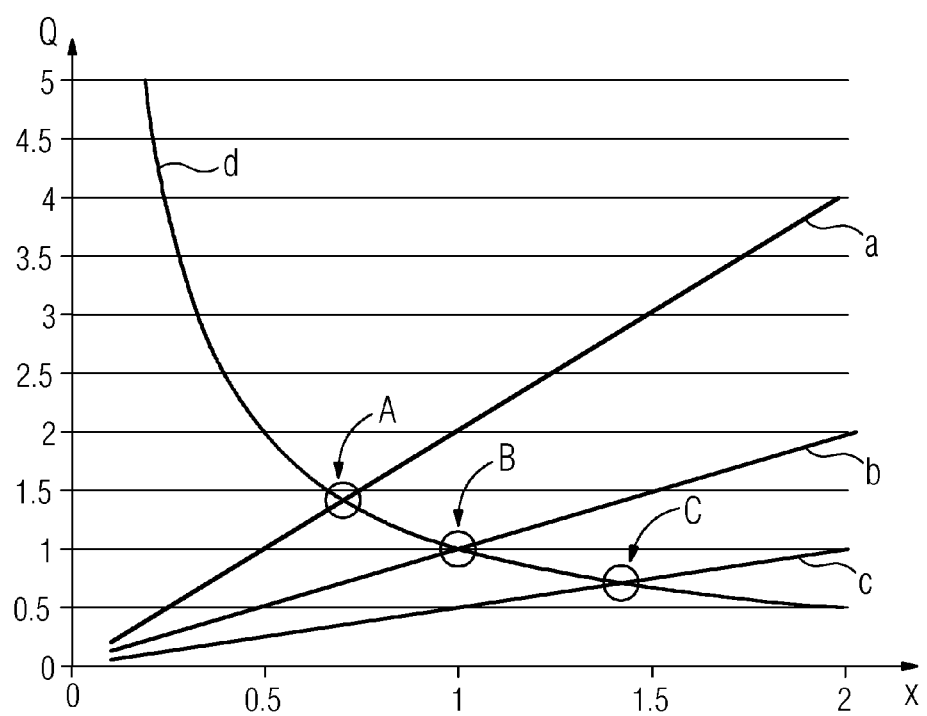
FIG. 2 depicts a graph that describes an exemplary connection between a change in an individual dose and the image quality of an assigned image signal.
Figure 3:
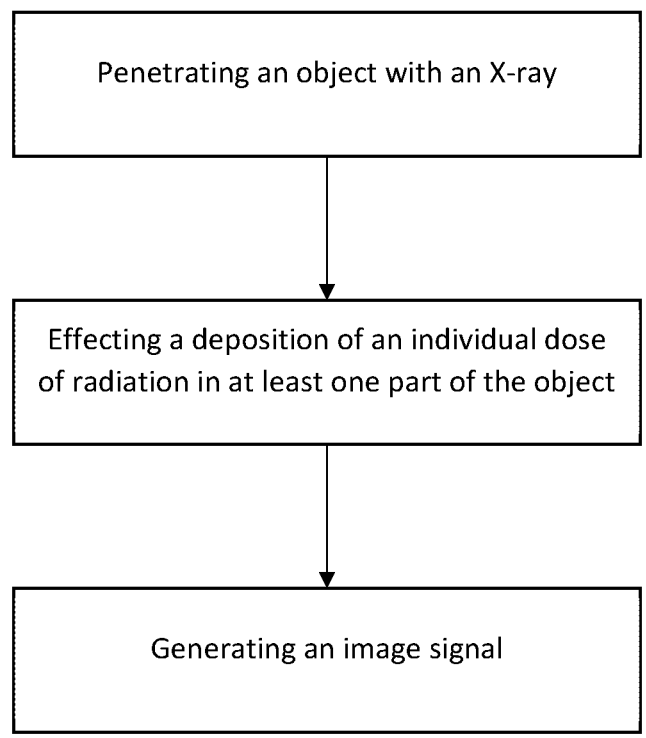
FIG. 3 depicts a flowchart of an exemplary embodiment of the method.

FIG. 1 depicts a cross-section of an exemplary object that is being irradiated by way of an exemplary variant of the method. In this cross-section, the object 3 is elliptical in shape. FIG. 1 represents an irradiation of the object 3 in a plurality, in the present case two, different positions 1, 2. In the first position 1 in this example, the object 3 is irradiated parallel to the short semi-axis of the ellipse formed by the object 3 in the cross-section; in the second position 2 perpendicular to the foregoing and parallel to the long semi-axis. Accordingly, in this case, a higher individual dose, which is deposited in the object 3, for example a patient's body, is to be expected in the second position 2 than in the first position 1 for an identical image quality Q (FIG. 2). This may be explained by the fact that if a homogeneous composition of the object 3 is assumed, a greater extent of an object in one direction goes hand in hand with a greater absorption of an X-ray that is passing through the object than is the case for a smaller extent along a direction of irradiation.

With respect to an image quality Q (FIG. 2) of a three-dimensional reconstruction, which is dependent on image signals captured in the present two positions 1, 2, the quality of the three-dimensional reconstruction remains unchanged on the basis of the error propagation if in the case of a decrease in the image quality of the one image signal, the image quality of the other image signal is correspondingly improved. In the example depicted, then, with respect to the required improvement in the image quality in the first position 1 for a constant quality of the three-dimensional reconstruction, a lower value of additional deposited individual dose has to be accepted than is saved by the corresponding lowering of the image quality of the image signal in the second position 2. Consequently, the sum of the individual doses, that is to say the total dose, is reduced in the example. At the same time, the share of the individual dose to be deposited in the first position 1 in the total dose is raised in the present case that, however, may also be effected independently of a change in the total dose. Thus, the total dose may also be kept constant or even raised and therefore, in the present case, with a raising of the share of the individual dose to be deposited in the first position 1 in the total dose, a better image quality be achieved than in the case of, in comparison to the starting position of a share of 50% of the total dose for example, a share of the individual dose to be deposited in the first position 1 in the total dose that is held constant.

On the assumption that the image quality Q (FIG. 2) of the three-dimensional construction, which is described by a signal-to-noise ratio for example, is subject to error propagation, the connection that Q is proportional to $1/[1/D_1+1/(y*D_1)]$ may be derived for an image quality Q of the three-dimensional construction. In this regard, $D_1$ is the individual dose in the first position 1 and y an equivalence factor that describes what multiple of the image quality of the first position 1 is obtained in the second position 2 if, in the second position 2, the amount of the individual dose $D_1$ in the first position 1 is accepted as a dose that is deposited or to be deposited. In this regard, y is predefined by the loss in transmitted intensity in the various positions, which is to say in the various directions of the angulations. In this regard, it is determined by the size of the X-ray absorption.

It is furthermore the case that the total dose D may be described by D is proportional to $D_1+x*D_1$. In this regard, it is the case that $x*D_1=D_2$, that is to say $D_2$ is the individual dose in the Position 2 and x the factor that describes a change in dose in position 2 proceeding from the position 1. From this it may be derived that, with respect to an optimal distribution of the total dose across the, in the present case, two different positions 1, 2, the condition $x=1/y$ has to be satisfied. This provides that if it is difficult, for example, to obtain a predefined image quality Q (FIG. 2) in a position, since this entails a very large individual dose, it is more favorable to multiply the actual individual dose in that position by the inverse of the additionally needed image quality and to deposit the correspondingly saved individual dose in other positions in which, for a given raising of the individual dose in the positions, a greater improvement in the image quality may be expected.

FIG. 2 depicts an exemplary graph that describes an exemplary connection between a change in an individual dose and the image quality of an associated image signal. This plots the image quality Q resulting for a change in dose in a predefined position against the corresponding dose change factor x. In this regard, the image quality Q is marked in arbitrary units in this case. In the case of an image quality of 1, the change in dose is standardized in the present case to that dose that has to be deposited in an object with a medium water equivalence value for an image signal with an image quality of $Q=1$.

The graph represents three straight lines a, b, c, running through the origin for different compositions of the irradiated object. The curves describe how an image quality behaves as a function of a change in individual dose for an object with a low water equivalence value ("water value") (curve a), a medium water equivalence value (curve b), and a high water equivalence value (curve c). Additionally, a hyperbola d, which represents the formula for the optimal dose, $x=1/y$, derived above, is marked in.

Due to the standardization of the change in dose, the curve b, which in fact describes the connection between an individual dose and the image quality Q for an object with a medium water equivalence value, has a slope of 1. If a material with a higher water equivalence value were then irradiated, due to a positional change into a second position for example, as is characterized by the curve c for example, then the same dose would only obtain an image quality of $Q=0.5$ at $x=1$. In order to achieve the previously achieved image quality of $Q=1$ in this new position, the individual dose would have to be correspondingly doubled to $x=2$. The derivation described above provides that this is not efficient. On the contrary, the optimal choice in this case is not to double the individual dose but just to raise it by around 45 percent, so that the image quality obtained achieves about 70 percent of the image quality in the first position with the medium water equivalence value. This corresponds to the intersection C between the curve c and the hyperbola d. The 55 percent of the individual dose saved in comparison to doubling the individual dose delivers a far greater improvement in the image quality Q in another position, the first position with the medium water equivalence value for example, which also follows from the greater slope of the curve b in comparison to the curve c.

Conversely, in another second position, at which a lower water equivalence value is present (as described by the curve a) for example, an image quality of $Q=2$ is achieved at an individual dose of $x=1$. However, the intersection A between the straight line a and the hyperbola d is once again the optimal choice, according to the consideration described above, with respect to a ratio of individual dose and resulting image quality. Accordingly, in an optimal manner in the example depicted, the individual dose is reduced at $x=0.7$ and therefore an image quality of around 1.45 achieved. The dynamic spread or the range of the image quality and the individual doses is therefore also reduced in the different positions with the present method in the present example.

This may be explained as follows: an initial strategy, for example, includes holding the respective individual doses constant in different positions. If this includes an individual dose of $x=1$ for example, then an image quality of $Q=1$ is correspondingly achieved for the image signal captured in the first position (curve b), an image with the image quality $Q=0.5$ in the second position corresponding to the curve c with the higher water equivalence value, and an image signal with the image quality $Q=2$ in the other second position. There is, therefore, a large range of image qualities for different irradiated materials or positions present here. In an alternative strategy in which the same image quality is obtained everywhere, the image quality $Q=1$ for example, a dose of $x=1$ is deposited in the first position, a dose of $x=2$ in the second position (curve c), and a dose of $x=0.5$ in the other second position (curve a). In the one case, therefore, the dose stays the same and the image quality fluctuates between 0.5 and 2; in the other case, the image quality $Q=1$ stays constant and the individual dose deposited fluctuates by a factor between 0.5 and 2. In the third, optimal, strategy, both image quality Q and also actual individual dose x vary respectively from 0.7 to 1.4, that is to say over a considerably smaller range.

For example, with respect to an object including a soft tissue, which is 5 millimeters thick and may have a homogeneous density distribution, the optimal strategy yields the following values: for a low water equivalence component of 230 millimeters, a tube voltage of 82 kilovolts, a tube current of 380 milliamperes, an exposure time of 5 milliseconds, prefiltering with 0.3 millimeters copper and corresponding to an emitter focus a detector input dose of 165 nanograys, and thus an image quality of $Q=4.9$ at an individual dose of 13.1; for a medium water equivalence component of 280 millimeters, a tube voltage of 92 kilovolts, a tube current of 340 milliamperes, an exposure time of 9 milliseconds, prefiltering with 0.3 millimeters copper and a detector input dose of 130 nanograys, and thus an image quality of $Q=2.5$ and an individual dose of 25.9; for a high water equivalence component of 330 millimeters, a tube voltage of 114 kilovolts, a tube current of 370 milliamperes, an exposure time of 10 milliseconds, prefiltering with 0.3 millimeters copper and a detector input dose of 140 nanograys, and thus an image quality of $Q=1.25$ and an individual dose of 51.2. In these three examples, the product of individual dose and image quality is around 64 in each case, that is to say constant, which provides that an optimal three-dimensional reconstruction of the object is achieved with the present parameters.

For example, with respect to an object including iodine, which is 1 millimeter thick and may have a homogeneous density distribution, the optimal strategy yields the following values: for a low water equivalence component of 230 millimeters, a tube voltage of 61 kilovolts, a tube current of 450 milliamperes, an exposure time of 10 milliseconds, prefiltering with 0.3 millimeters copper and a detector input dose of 25 nanograys, and thus an image quality of Q=5.7 and an individual dose of 5.9; for a medium water equivalence component of 280 millimeters, a tube voltage of 72 kilovolts, a tube current of 430 milliamperes, an exposure time of 10 milliseconds, prefiltering with 0.3 millimeters copper and a detector input dose of 35 nanograys, and thus an image quality of Q=2.5 and an individual dose of 13.3; for a high water equivalence component of 330 millimeters, a tube voltage of 95 kilovolts, a tube current of 330 milliamperes, an exposure time of 10 milliseconds, prefiltering with 0.3 millimeters copper and a detector input dose of 65 nanograys, and thus an image quality of Q=1 and an individual dose of 33.3. In this example, the product of image quality and individual dose then produces around 33 in each case, so that the total dose deposited or to be deposited is distributed optimally across the three positions here also, so that for a given total dose, the best possible image quality is provided for the three-dimensional reconstruction derived from these three individual corresponding image signals. In the last two examples, the image quality Q and the individual dose are entered in arbitrary units in each case.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating a computed tomograph, the method comprising:
    penetrating an object with an X-ray from a plurality of positions;
    effecting, at each position of the plurality of positions, a deposition of an individual dose of radiation in at least one part of the object, wherein the individual doses add up to a total dose of radiation; and
    generating an image signal, via a detector, at each position of the plurality of positions, by way of a transmitted intensity of the X-ray,
    wherein a plurality of exposure parameters, which influence an image quality of the image signal, are set individually for each position of the plurality of positions, wherein the exposure parameters for each position of the plurality of positions are selected such that a respective product of the individual dose and a measure for the image quality is identical for each position of the plurality of positions,
    wherein individual doses for respective positions of the plurality of positions are configured to be: (1) raised when a raising provides a greater improvement in the image quality than in another position, or (2) lowered when a lowering provides a smaller deterioration in the image quality than in another position, and
    wherein the total dose of radiation does not exceed a predetermined value such than when an individual dose is raised in a specific position, at least one additional individual dose is lowered in at least one separate position.

2. The method as claimed in claim 1, wherein the individual doses are raised or lowered starting from a predetermined default setting at which identical values are selected for the exposure parameters for each position of the plurality of positions.

3. The method as claimed in claim 2, wherein a signal-to-noise ratio is selected as a measure for the image quality.

4. The method as claimed in claim 2, wherein one exposure parameter of the plurality of exposure parameters is a tube voltage, a tube current, an exposure time, or a combination thereof.

5. The method as claimed in claim 1, wherein the individual doses to be deposited are set with account being taken of weighting factors for specific tissues.

6. The method as claimed in claim 5, wherein the individual doses to be deposited are set with account being taken of an anatomy of a patient.

7. The method as claimed in claim 5, wherein the specific tissues comprise organs.

8. The method as claimed in claim 1, wherein a signal-to-noise ratio is selected as a measure for the image quality.

9. The method as claimed in claim 1, wherein a square of a signal-to-noise ratio is selected as a measure for the image quality.

10. The method as claimed in claim 1, wherein one exposure parameter of the plurality of exposure parameters is a tube voltage, a tube current, an exposure time, or a combination thereof.

11. The method as claimed in claim 1, wherein the individual doses to be deposited are set with account being taken of an anatomy of a patient.

* * * * *